United States Patent
Brownlee

[11] Patent Number: 5,814,076
[45] Date of Patent: Sep. 29, 1998

[54] APPARATUS FOR IMPROVED CARDIAC PACING AND SENSING USING EXTRACARDIAC INDIFFERENT ELECTRODE CONFIGURATIONS

[75] Inventor: Robert R. Brownlee, Ormond Beach, Fla.

[73] Assignee: Cardiac Control Systems, Inc., Palm Coast, Fla.

[21] Appl. No.: 594,887

[22] Filed: Feb. 9, 1996

[51] Int. Cl.$^6$ .................................................... A61N 1/362
[52] U.S. Cl. ............................... 607/9; 607/37; 128/901
[58] Field of Search .................................. 607/9, 14, 15, 607/4, 5, 121, 119, 116, 36, 37; 128/901

[56] References Cited

U.S. PATENT DOCUMENTS

| | | | |
|---|---|---|---|
| 3,893,461 | 7/1975 | Preston | 128/419 P |
| 3,915,174 | 10/1975 | Preston | 128/419 P |
| 4,010,755 | 3/1977 | Preston | 128/404 |
| 4,026,302 | 5/1977 | Grayzel | 128/418 |
| 4,369,791 | 1/1983 | Friedman | 607/36 |
| 4,387,717 | 6/1983 | Brownlee et al. | 607/9 |
| 4,401,119 | 8/1983 | Herpers | 607/9 |
| 4,549,548 | 10/1985 | Wittkampf et al. | 607/36 |
| 4,602,637 | 7/1986 | Elmqvist et al. | 607/36 |
| 5,107,834 | 4/1992 | Ideker et al. | 607/5 |
| 5,209,229 | 5/1993 | Gilli | 128/419 D |
| 5,235,978 | 8/1993 | Hirschberg et al. | 607/5 |
| 5,313,953 | 5/1994 | Yomtov et al. | 607/36 |
| 5,360,442 | 11/1994 | Dahl et al. | 607/129 |
| 5,376,103 | 12/1994 | Anderson et al. | 607/52 |
| 5,385,574 | 1/1995 | Hauser et al. | 607/14 |
| 5,522,855 | 6/1996 | Hoegnelid | 607/9 |
| 5,529,579 | 6/1996 | Alt et al. | 607/36 |
| 5,531,766 | 7/1996 | Kroll et al. | 607/9 |

*Primary Examiner*—Marvin M. Lateef
*Assistant Examiner*—Kennedy J. Schaetzle
*Attorney, Agent, or Firm*—Kerkam, Stowell, Kondracki & Clarke; Dennis P. Clarke

[57] ABSTRACT

The present invention provides an improved extracardiac indifferent electrode configuration for implantable medical devices that overcomes the deficiencies of known unipolar and bipolar cardiac sensing and pacing systems. In particular, the present invention provides an indifferent electrode configuration wherein a subcutaneous extracardiac electrode is advantageously positioned so as to provide a truly indifferent return or reference electrode that does not inadvertently stimulate torso muscle and is not subject to detecting myopotentials generated by adjacent torso muscle. In addition, by being placed outside the heart, the indifferent electrode allows the intracardiac catheter to maintain a low profile, i.e., allows the catheter to be as small as possible, and does not generate metallic ions or cause degradation of catheter materials by generating such ions.

11 Claims, 5 Drawing Sheets

APPARATUS FOR IMPROVED CARDIAC PACING AND SENSING USING EXTRACARDIAC INDIFFERENT ELECTRODE CONFIGURATIONS

FIELD OF THE INVENTION

The present invention relates to a method and apparatus for improved performance for implantable medical devices, using implantable indifferent electrode configurations. In particular, the invention provides a method and apparatus for improved cardiac pacing and sensing using an extracardiac indifferent electrode configuration that utilizes a subcutaneous indifferent electrode, instead of the device housing, as a return path for signals of an implantable pacemaker device.

BACKGROUND OF THE INVENTION

Cardiac pacemakers, in general, provide stimulating pulses to, and receive sensing signals from, cardiac tissue via electrodes that are strategically placed in the heart cavity. The electrodes are conventionally housed in a catheter which is introduced into the heart cavity transvenously. Typically, there are two basic forms of catheters employed in cardiac pacing systems. The first of these is called a unipolar catheter. Unipolar catheters, in their simplest form, contain one pacing electrode housed distally on the catheter. The pacemaker's pulse generator and sensing system are connected to the electrode via an insulated conductor, i.e., the catheter, that is inserted into a selected chamber of the heart generally through right heart venous access. Completion of the circuit for pacing and sensing generally requires a second system electrode. In unipolar systems, the pacemaker's metallic housing generally serves as the second, or return, electrode. This second electrode, which is not deployed inside a heart chamber, is generally termed an indifferent electrode. However, the term indifferent electrode, when used in the above manner, is a misnomer, in that this electrode can stimulate torso muscle cells adjacent to the electrode, i.e., the metallic pacemaker housing. Stimulation of muscle cells adjacent to the electrode is a major disadvantage of systems that use the pacemaker housing as the "indifferent" electrode. True indifferent electrodes, as used in electrocardiographic systems and in some types of pacemaker systems, cooperate with two or more electrodes, and are generally referred to as reference electrodes.

Another common disadvantage of systems that use the pacemaker's housing to serve as the "indifferent" electrode is that myopotentials generated by torso muscle activity may fall within the vector field between the "indifferent" extracardiac electrode and the "active" intracardiac electrode. When these myopotentials fall within the vector field between the active and indifferent electrodes, the myopotentials can be detected by the pacemaker sensing circuit and tend to disrupt normal pacing and sensing functions of the system. Accordingly, the so-called "indifferent" electrode is not indifferent to the myopotentials, and becomes "active" when it inadvertently stimulates adjacent muscle during delivery of pace pulses from the pacemaker to the intracardiac, i.e., active, electrode.

A variety of methods and configurations have evolved over time to improve unipolar pacing systems and overcome the problems noted above. Among the most popular of these systems is the bipolar pacing system. In bipolar systems, the intracardiac transvenous pacing catheter houses two electrodes. Each electrode is connected to the pacemaker independently of the other through insulated conductors housed in the same catheter body. The second electrode of bipolar systems is also placed inside the heart chamber and serves as the circuit return connection for the pacing and sensing functions of that chamber. Because the second electrode is no longer adjacent torso muscle, the problem of inadvertent stimulation thereof is eliminated. Additionally, because there is no intervening torso muscle between the two intracardiac electrodes, the vector magnitude of myopotentials is reduced to levels that are insufficient to cause disruption of normal pacemaker function.

However, there are several problems associated with the use of transvenous intracardiac bipolar electrode systems. Among these problems is that catheters used in bipolar systems are, by their very nature, larger than catheters used in unipolar systems, because of the requirement in bipolar systems of having two independent insulated conductors disposed within the catheter. This problem is further exacerbated with the advent of bipolar, dual-chamber, single-catheter pacing systems in which four independently insulated conductors are required to be housed in a common catheter body. In dual-chamber bipolar systems, two of the conductors serve as a pair of bipolar electrodes in the ventricular chamber of the heart, while another two conductors serve as the pair of electrodes for the atrial chamber of the heart. In addition to the size disadvantage and the difficulties associated with implanting large four-conductor catheters, these four-conductor catheters are very expensive to manufacture.

Another disadvantage associated with bipolar systems is that many of the biocompatible elastomer materials used for the catheter insulation are susceptible to attack by metallic ions released from the metallic conductors when they are employed in bipolar pacing catheters. The metallic ion generation, and subsequent elastomer degradation caused by ion attack, is dramatically increased by the large gradient electric field developed across the insulative barrier between the two tightly-spaced conductors when housed in the common catheter body of bipolar pacing systems.

SUMMARY OF THE INVENTION

The present invention provides an improved extracardiac indifferent electrode configuration for implantable medical devices that overcomes the deficiencies of known unipolar and bipolar cardiac sensing and pacing systems. In particular, the present invention provides an indifferent electrode configuration wherein a subcutaneous extracardiac electrode is advantageously positioned so as to provide a truly indifferent return or reference electrode that does not inadvertently stimulate torso muscle and is not subject to detecting myopotentials generated by adjacent torso muscle. In addition, by being placed outside the heart, the indifferent electrode allows the intracardiac catheter to maintain a low profile, i.e., allows the catheter to be as small as possible, and does not generate metallic ions or cause degradation of catheter materials by generating such ions.

Accordingly, it is an object of the present invention to provide an indifferent electrode configuration for an implantable medical device that does not suffer the disadvantages of known systems.

It is another object of the present invention to provide an indifferent electrode configuration, wherein the indifferent electrode is remote from the metallic housing of the implantable medical device.

It is also an object of the present invention to provide indifferent electrode geometries that mitigate torso muscle stimulation.

It is yet another object of the present invention to provide an indifferent electrode configuration that mitigates myopotential disruption of pacemaker function.

Another object of the present invention is to provide indifferent electrode orientations relative to intracardiac electrodes that enhance the detection of the appropriate cardiac signals and lower the energy required to stimulate cardiac muscle by concentrating stimulation current through localized cardiac tissue.

It is an also an object of the present invention to avoid elastomer degradation by metallic ion attack by providing an indifferent electrode using an independent catheter for the circuit return path.

These and other objects, and their attendant advantages, are achieved by the present invention, which provides an indifferent electrode configuration for an implantable medical device, comprising: a first intracardiac electrode connected to a first circuit of the implantable medical device, said first electrode being positioned in a predetermined chamber of the heart and adjacent an inner surface thereof; a first extracardiac electrode connectable to said first circuit of the implantable medical device and being positioned subcutaneously to a position adjacent an outer wall of the heart in an area of reduced torso muscle; and a second extracardiac electrode serving as a circuit ground and being positionable in a predetermined subcutaneous position outside the heart.

In a preferred embodiment of the present invention, an indifferent electrode configuration for an implantable medical device is provided wherein the indifferent electrode comprises two electrodes disposed subcutaneously and outside the heart to enhance the sensing and pacing functions of the implantable medical device. In this embodiment a second indifferent electrode is employed which acts as a reference electrode in place of the metallic housing of the implantable medical device. The second indifferent electrode also acts as the indifferent electrode for pacing in both chambers of the heart and for sensing the activity of the ventricle.

BRIEF DESCRIPTION OF THE DRAWINGS

The invention will be described in detail herein with reference to the following drawings in which like reference numerals refer to like elements throughout the several views, and wherein.

DETAILED DESCRIPTION OF THE PREFERRED EMBODIMENTS

Figure 1:
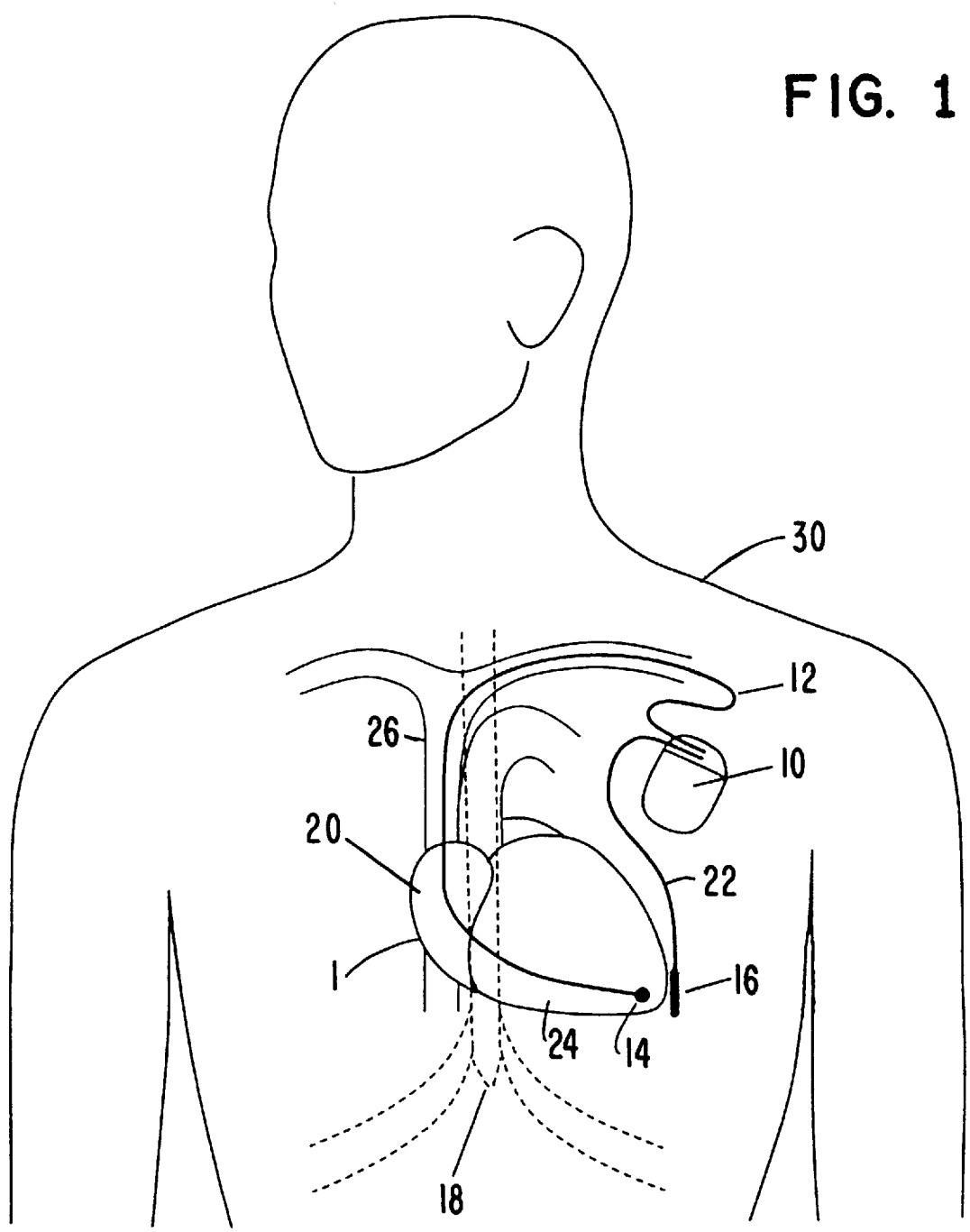
FIG. 1 is a view of one embodiment of the indifferent electrode configuration in a body, together with the implantable medical device, wherein the indifferent electrode is deployed subcutaneously and is used in conjunction with a unipolar ventricular electrode.

FIG. 1 shows a unipolar catheter 12 having a single electrode 14 distally deployed at the apex of the right ventricle 24 of the heart 1. The unipolar catheter 12 is connected on one end to an implanted medical device 10, such as, for example, a cardiac pacemaker. At the other end of the unipolar catheter 12, is disposed an electrode 14 which is deployed in proximity to the apex of the right ventricle 24 of the heart 1. In an exemplary fashion, the catheter 12 extends from the pacemaker 10 through the superior vena cava 26 and the right atrium 20 of the heart 1, and into the right ventricle 24. An indifferent electrode 16 is also deployed in the body 30 of patient. However, the indifferent electrode 16 is deployed subcutaneously in an area adjacent an outer wall of the right ventricle 24 in a position substantially overlying the intracardiac electrode 14. The indifferent electrode 16 need not overlie the intracardiac electrode 14 exactly, but should be positioned so as to improve the sensed ratio of desired signals from the ventricle 24 to undesired signals from torso muscles, i.e., myopotentials. The positioning of the indifferent electrode 16 relative to the intracardiac electrode 14 will be easily determined by one of ordinary skill in the art. The indifferent electrode 16 is connected to the cardiac pacemaker 10 by a second catheter 22, which is also preferably positioned to be subcutaneously deployed.

As discussed above, the site for positioning the indifferent electrode 16 is selected such that the intracardiac electrode 14 and the indifferent electrode 16 form an electrode pair that tend to become bipolarized relative to the improvement of the sensed ratio of desired signals from the ventricle 24 to undesired signals from torso muscles, i.e., myopotentials. The large pectoral muscle mass (not shown), the normal site of conventional indifferent electrodes, is a large interfering signal generator that is activated by upper arm motion, or when flexed even without motion, such as, for example, as in isometric exercise. The intercostal and transverse thoracic muscles (not shown), in contrast to the pectoral muscle mass, are much smaller and are less likely to generate signals sufficient to be detected by pacemaker systems. Accordingly, it is preferable to locate the indifferent electrode 16 at a site closer to the intercostal and transverse thoracic muscles and relatively remote from the pectoral muscle mass. Inadvertent stimulation of muscle may also occur when using an indifferent electrode. This problem is especially troublesome when using the metallic case of the pacemaker 10 as an indifferent electrode. However, by placing the indifferent electrode 16 of the present invention remotely from the pectoral muscle mass and in proximity of the intercostal and transverse thoracic muscles, inadvertent muscle stimulation, if it occurred, would also be less troublesome to the patient compared to stimulation of the relatively large pectoral muscle mass. Movement of the subcutaneous indifferent electrode 16 to a remote site in the region of the sternum 18 would also further reduce the potential for muscle signal interference and inadvertent muscle stimulation, as this region is substantially devoid of muscle.

Figure 2:
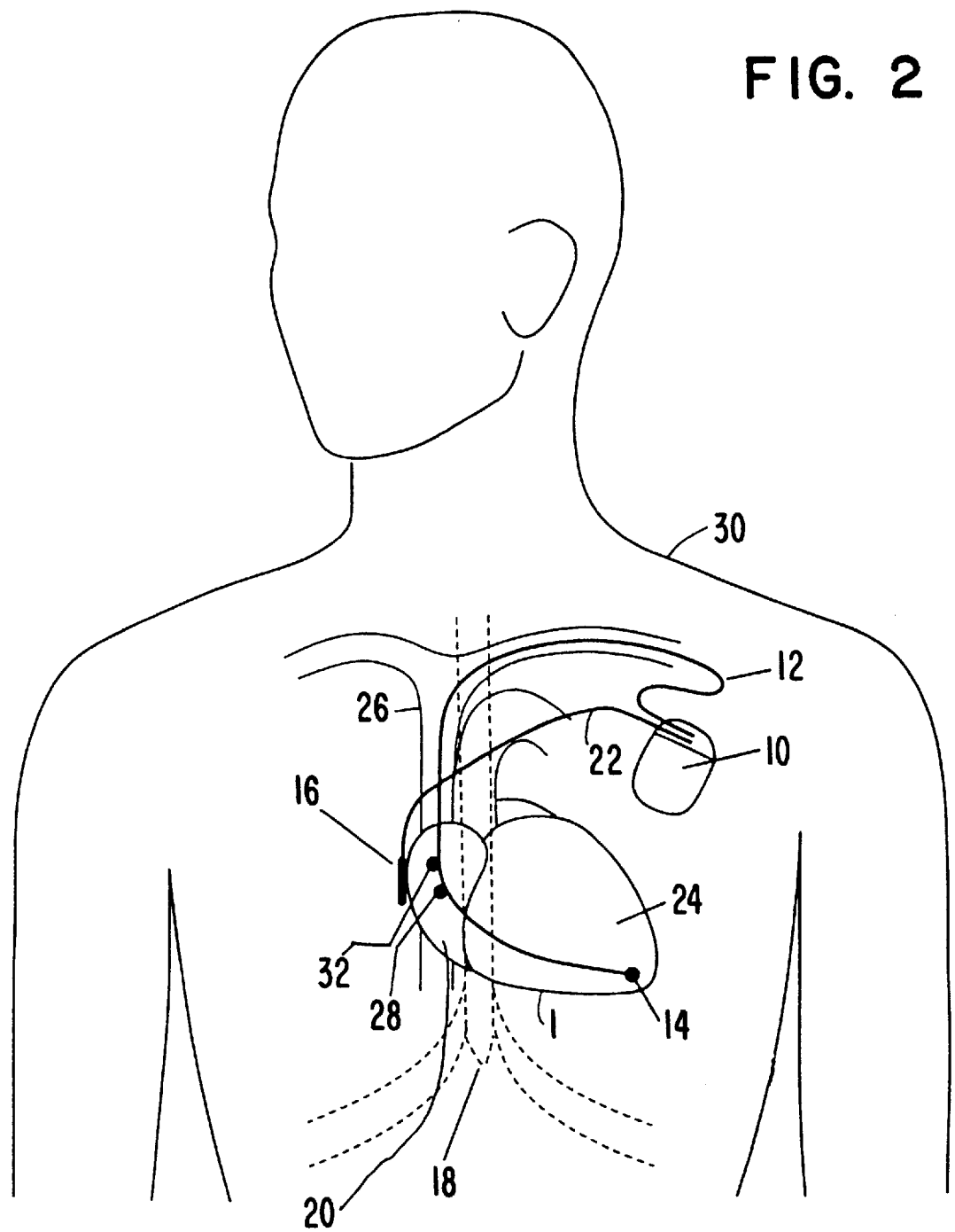
FIG. 2 is a view of a second embodiment of the indifferent electrode configuration in a body, together with the implantable medical device, wherein the indifferent electrode deployed subcutaneously and is used to enhance the detection of atrial depolarizations.
Figure 5:
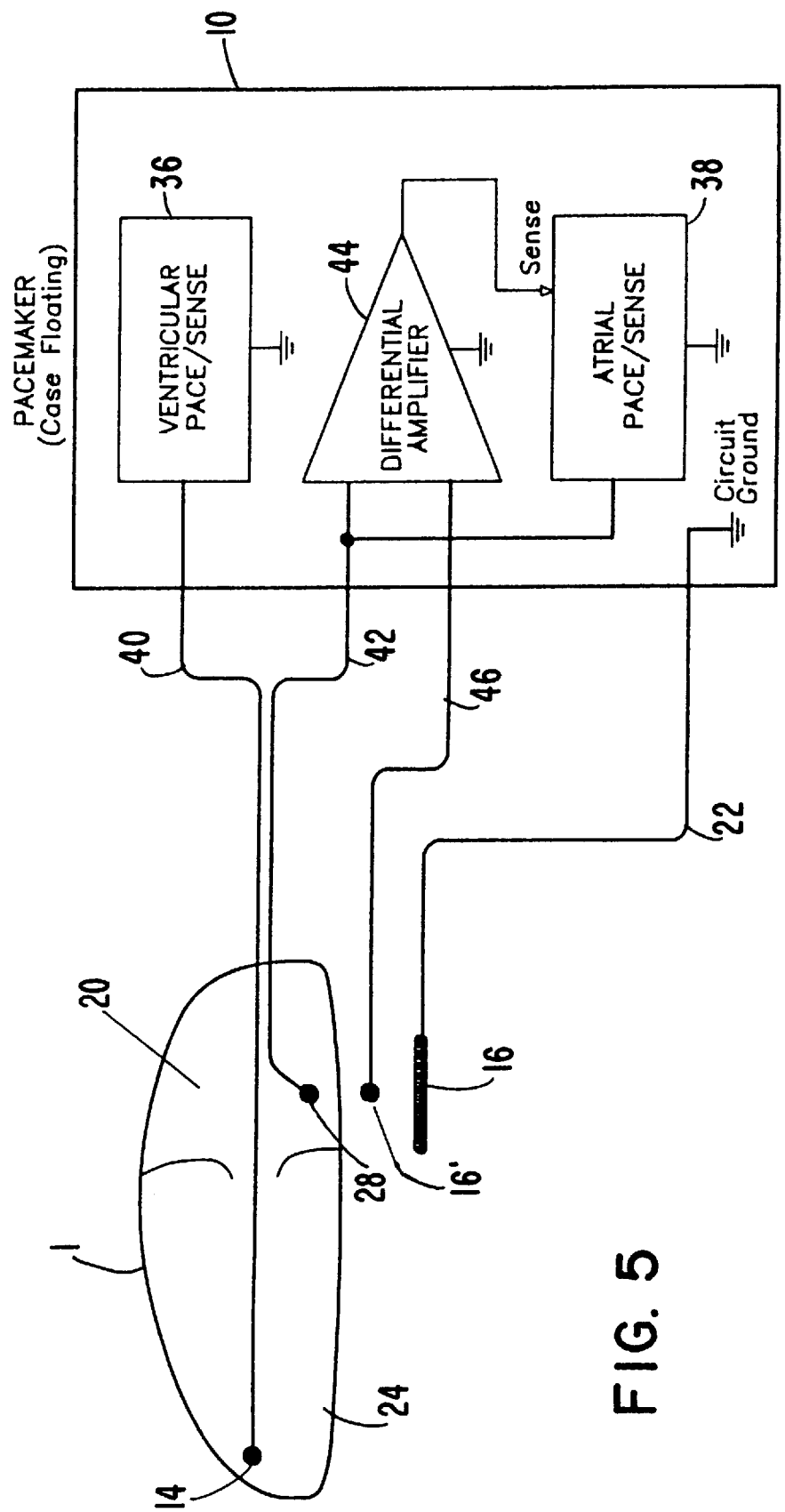
FIG. 5 is a schematic view of a third embodiment of the indifferent electrode configuration, in a body, together with the implantable medical device, wherein the indifferent electrode configuration comprises two different indifferent electrodes.

FIG. 2 shows the use of a remote site for indifferent electrode 16 chosen specifically for enhancement of the detection of atrial depolarization signals, and to reduce the energy required to stimulate the atrial chamber 20 of the heart 1. Specifically, the configuration of FIG. 2 includes a single unipolar intracardiac catheter 12, which is deployed to sense and pace both the atrial chamber 20 and ventricular chamber 24 of the heart 1. The catheter 12 includes a pair of atrial sense and pace electrodes 28, 32 and a single ventricular electrode 14. The atrial electrode pair 28, 32 are disposed adjacent an inner wall of the atrium 20, while the ventricular electrode 14 is disposed in an area near the apex of the ventricle 24. The single unipolar intracardiac catheter 12 of FIG. 2 requires the use of only two insulated catheters (not shown) to carry the electrodes. The indifferent electrode 16, connected to the pacemaker 10 by a catheter 22, is disposed in a region adjacent the outer wall of the atrium 20 and substantially overlying the atrial electrode pair 28, 32. The atrial chamber 20 is the most difficult to deal with because detection of the small atrial depolarization signals and stimulation of atrial cardiac muscle are generally more problematic than sensing and pacing ventricular muscle. Accordingly, as shown in FIG. 2, the indifferent electrode 16 is disposed at a torso location to cooperate principally with the atrial electrode pair 28, 32 so as to reduce detection of myopotentials and ventricular signals in the atrial sensing channel (not shown) of the pacemaker 10. An alternative use of the indifferent electrode 16 in the configuration shown in FIG. 2 would be to employ the electrode 16 only as a sensing indifferent electrode and use either the pacemaker case or an additional remote indifferent electrode for the return path for stimulation and/or for serving as a true reference electrode for differential atrial signal processing as shown in FIG. 5.

The size, shape and composition of extracardiac electrodes are all factors that can influence their performance in various applications. For example, when an indifferent electrode is employed to prevent muscle stimulation, the electrode is typically made to be relatively large to reduce the current density to a level which is below the stimulation thresholds of adjacent muscles. Additionally, relatively large extracardiac electrodes tend to reduce the electrode tissue interface impedance so that maximum delivered energy from the pacemaker is expended at the intracardiac electrode site. For example, intracardiac stimulating electrodes, typically having sizes in the 10 mm$^2$ range, should have cooperating extracardiac indifferent electrodes that are in the range of 100 mm$^2$ (1 cm$^2$), i.e., in the range of ten times larger than the intracardiac electrode, or larger, to prevent significant loss of energy at the indifferent electrode site. A size of 100 mm$^2$ is smaller than typical pacemaker housings and could be formed in shapes that are compatible with insertion through a subcutaneous tunnel to, for example, a sternum location that is essentially devoid of torso muscle, as discussed above. A metallic cylinder having a diameter in the range of two to three millimeters and a length in the range of one to two centimeters is illustrative of an electrode that would provide sufficient surface area for the pacing function, yet would be small enough to tunnel subcutaneously from the pacemaker to the desired remote location. Porous insulative surface treatments may also be used with the extracardiac indifferent electrodes to assure uniform distribution of current and to prevent direct metallic contact with any adjacent torso muscle. Use of these surface treatments would serve to mitigate the potential for local torso muscle stimulation. For example, the indifferent electrode may be coated with an elastomeric material having microscopic holes formed therein, thereby providing the required conductivity in a body fluid environment, while spacing the metallic electrode from direct contact with excitable muscle.

For extracardiac electrodes that are used only for sensing, as will be shown with respect to the configurations shown in FIGS. 4 and 5 below, the electrode size should preferably be similar to the size of the intracardiac electrode with which it is to cooperate to provide balance in a differential processing environment, which is used in the sensing configurations.

Figure 3:
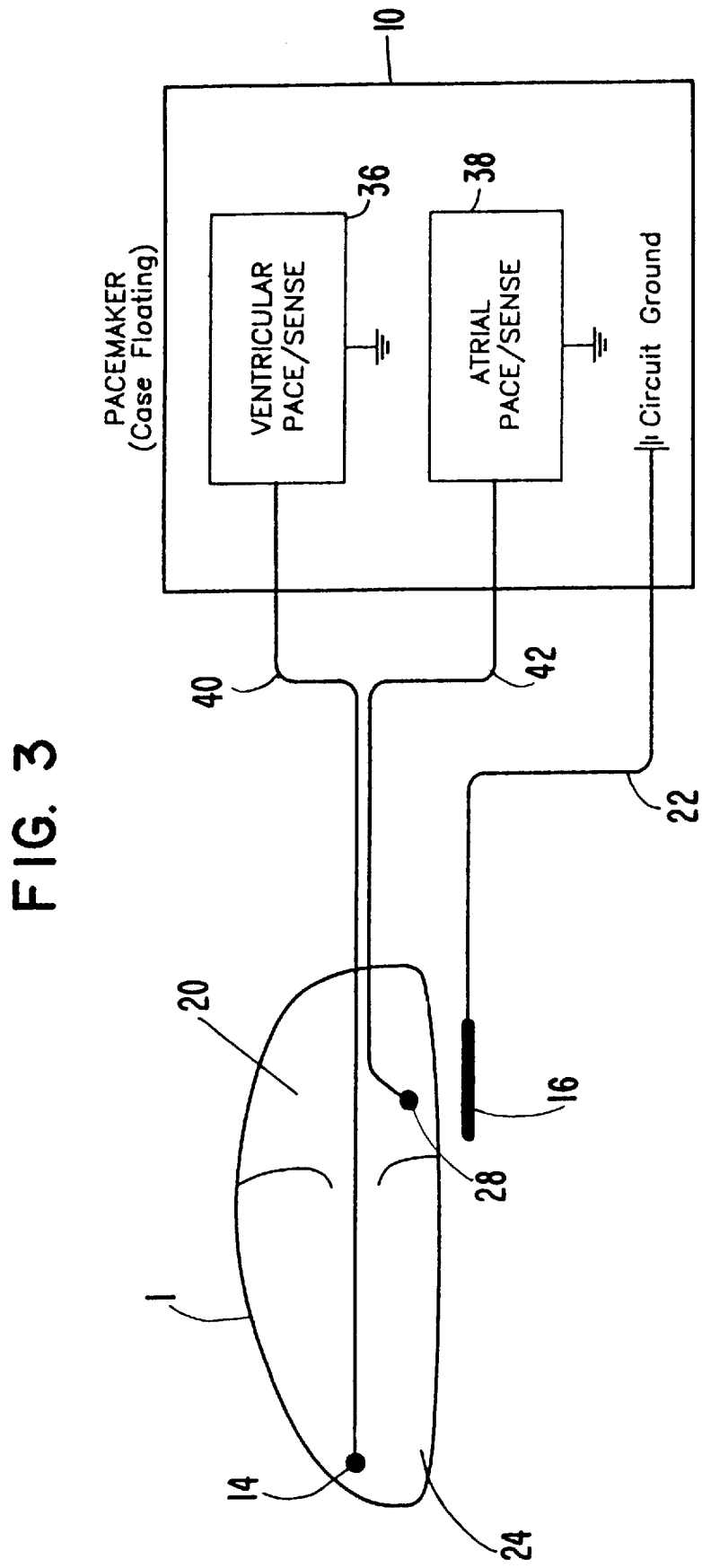
FIG. 3 is a schematic view of the pacemaker circuits using the indifferent electrode configuration shown in FIG. 2.

FIG. 3 schematically depicts an intracardiac unipolar ventricular electrode 14 and an intracardiac unipolar atrial electrode 28 employed in the respective chambers 24, 20 of the heart 1. The configuration shown in FIG. 3 may comprise either a single transvenous catheter or, as shown in FIG. 3, two separate transvenous catheters 40, 42 for connecting the unipolar intracardiac electrodes to the pacemaker 10. The extracardiac indifferent electrode 16 is connected to the pacemaker 10 and deployed through a separate catheter 22 to serve as the indifferent electrode for pacing and sensing both chambers of the heart 1. Because the indifferent electrode 16 is remote from the pacemaker housing, it can be conveniently located in closer proximity to the intracardiac atrial electrode 28, preferably overlying the electrode 28, to improve the performance of that electrode for pacing and sensing the atrium 20. The extracardiac indifferent electrode 16 also serves as the circuit ground for the configuration, thereby reducing myopotential interference and the probability of inadvertent torso muscle stimulation.

Figure 4:
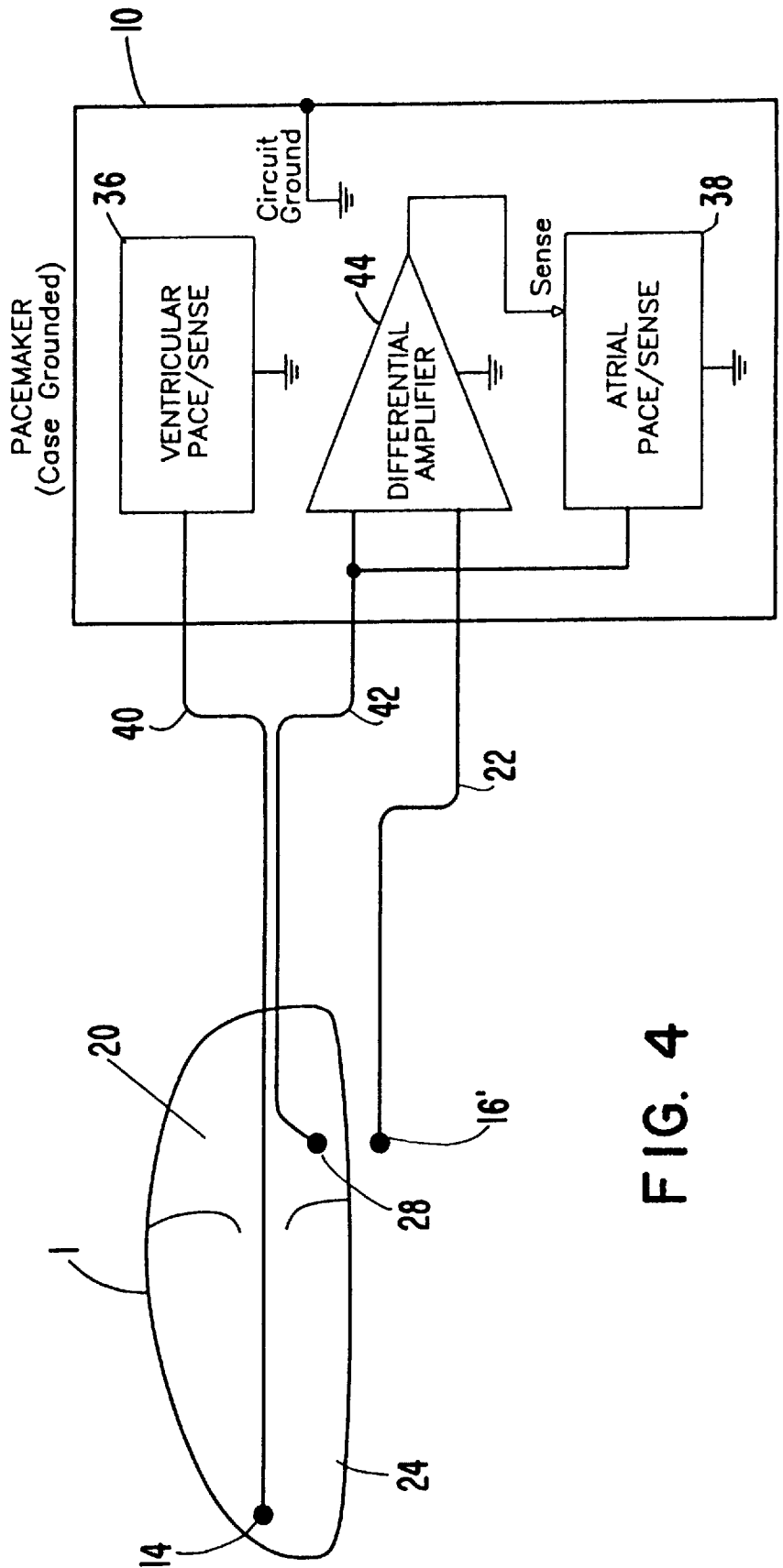
FIG. 4 is a schematic view of an alternative pacemaker processing configuration using the indifferent electrode configuration shown in FIG. 2.

FIG. 4 depicts a configuration, wherein the extracardiac electrode 16' is used for improving only the sensing performance of an intracardiac atrial electrode 38. As shown in FIG. 4, the pacemaker case is not only used as the indifferent electrode for pacing and sensing the ventricle and for pacing the atrium, but also acts as a true reference electrode for one intracardiac electrode and one extracardiac electrode whose signals are cooperatively processed in a differential amplifier 44. The mechanism of this configuration is, in effect, one that bipolarizes atrial sensing using an extracardiac electrode 16', while providing the benefits of unipolar transvenous catheters for deployment of unipolar intracardiac electrodes. As discussed above, when using an extracardiac electrode 16' for only sensing the signals of the atrium 20, as shown in FIG. 4, an electrode having roughly the same size as the intracardiac electrode 28, with which the extracardiac electrode 16' is cooperating, is preferred. In the differential processing scheme depicted in FIG. 4, the ventricular intracardiac electrode 14 is connected to a ventricular pacing and sensing circuit 36 of the pacemaker 10 via catheter 40. In addition, the atrial intracardiac electrode 28 is connected by its catheter 42 to both a differential amplifier 44 and an atrial sense and pace circuit 38 of the pacemaker 10. To enhance atrial signal detection, the extracardiac electrode 16' is connected via its catheter 22 to the differential amplifier 44. The differential amplifier 44 detects the difference signal between the atrial electrode 28 and the extracardiac electrode 16' to generate a sense signal. The improved sense signal generated by the differential amplifier 44 is then fed to the atrial pace-and-sense circuit 38, which, in turn, uses the improved sense signal to provide improved pacing and sensing data to the pacemaker 10 and to provide improved pacing and sensing signals to and from the atrial electrode 28.

A preferred embodiment of the present invention, using two extracardiac electrodes 16, 16' for providing combinational features that enhance the sensing and pacing properties of present invention, is shown in FIG. 5. The embodiment shown in FIG. 5 uses two extracardiac electrodes 16, 16'. The second extracardiac electrode 16 is used as the indifferent electrode for pacing in both the ventricular chamber 24 and atrial chamber 20 of the heart 1. The second extracardiac electrode 16 is also used for sensing in the ventricle 24. The first extracardiac electrode 16' is employed to provide improved sensing of the atrium 20, as set forth above with respect to FIG. 4. Physically separating the two extracardiac electrodes 16, 16' allows separate optimum placement for the specific function of each of the electrodes. For example, the smaller extracardiac electrode 16' can be positioned to cooperate best with the intracardiac atrial electrode 28 for sensing atrial signals, while the second extracardiac electrode 16 can be optimally positioned to be the indifferent electrode, thereby avoiding inadvertent torso muscle stimulation. In operation, the configuration of FIG. 5 uses a small first extracardiac electrode 16' connected to the differential amplifier 44 of the pacemaker 10 by an independent catheter 46. The small extracardiac electrode 16' is positioned for optimal sensing of the atrial chamber 20 of the heart 1. The second extracardiac electrode 16 serves as the circuit ground and is positioned to provide optimal pacing and sensing for the ventricular chamber 24 and sensing for the atrial chamber 20. The second extracardiac electrode is connected to the pacemaker 10 by an independent catheter 22. The ventricular intracardiac electrode 14 is connected to the ventricular pace-and-sense circuit 36 of the pacemaker 10 by its own catheter 40. The second extracardiac electrode 16 serves as the indifferent electrode for the ventricular electrode 14. The atrial intracardiac electrode 28 is connected to both the differential amplifier 44 and the atrial pace-and-sense circuit 38 of the pacemaker 10 via its independent catheter 42. The first extracardiac electrode 16' is also connected to the differential amplifier 44. The differential amplifier 44 provides an improved sense signal, i.e., the difference signal between the atrial electrode 28 and the first extracardiac electrode 16', to the atrial sense and pace circuit 38. The second extracardiac electrode 16 serves as the reference electrode for the atrial sensing portion of the circuit. The sizes and shapes of the two extracardiac electrodes are discussed above. The first extracardiac electrode 16' will have a size preferably in the range of the size of the atrial intracardiac electrode 28, while the second extracardiac electrode 16 will be approximately ten times the size of the intracardiac electrodes 14, 28. It should also be noted that the dual extracardiac electrode configuration shown in FIG. 5 will also provide the advantages discussed if only atrial signal processing and pacing are desired, i.e., without a ventricular electrode or ventricular pacing and sensing.

Beyond the embodiments described above with respect to FIGS. 1–5, it is also contemplated that indifferent electrodes of the type disclosed and claimed herein could also be deployed transvenously into and near the active electrodes in their respective heart chambers, but on a separate catheter than the active electrode catheter. Although this arrangement would require insertion of an additional catheter into the venous system, the intracardiac indifferent electrode position would not be critical and could, in fact, float in the blood pool to provide the required functionality. The only major concern during implantation would be to assure avoidance of contact with the active electrodes.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative, not limiting. Various changes may be made without departing from the true spirit and full scope of the invention, as defined in the following claims.

What is claimed is:

1. An apparatus for sensing electrical heart signals and for applying a pacing signal across the heart muscle of a person, said apparatus comprising:

a pacemaker constructed to be implanted adjacent a pectoral muscle mass of said person;

a first intracardiac catheter connected to said pacemaker and including a first intracardiac electrode positioned in a predetermined chamber of the heart; and a first extracardiac catheter connected to said pacemaker and including a first indifferent electrode thereon, said first extracardiac catheter having a length which enables said indifferent electrode to be positioned subcutaneously on said person at a location which is remote from said pectoral muscle mass to reduce myopotential sensing.

2. The apparatus as defined in claim 1, wherein said first extracardiac catheter is constructed to enable said first indifferent electrode to be located adjacent intercostal and transverse thoracic muscles of said person.

3. The apparatus as defined in claim 1, wherein said first extracardiac catheter is constructed to enable said first indifferent electrode to be located adjacent a sternum of said person.

4. The apparatus as defined in claim 1, wherein said first extracardiac catheter is constructed to enable said first indifferent electrode to be located near enough to said first intracardiac electrode to cause the first indifferent electrode and first intracardiac electrode to form an electrode pair which bipolarizes the operation of said apparatus.

5. The apparatus as defined in claim 1, wherein said pacemaker includes differential processing means for generating an improved sense signal, said first intracardiac electrode and said first indifferent electrode being connected with said differential processing means.

6. An apparatus for sensing electrical heart signals and for applying a pacing signal across the heart muscle of a person, said apparatus comprising:

a pacemaker constructed to be implanted in said person;

a first intracardiac catheter connected to said pacemaker and including a first intracardiac electrode positioned in a predetermined chamber of the heart; and a first extracardiac catheter connected to said pacemaker and including a first indifferent electrode thereon, said first extracardiac catheter having a length which enables said indifferent electrode to be positioned subcutaneously on said person at a location which is remote from said pacemaker and reduces myopotential sensing.

7. The apparatus as defined in claim 6, wherein said first intracardiac electrode is a ventricular electrode and said apparatus further includes a pair of intracardiac atrial sense and pace electrodes, and further wherein said first extracardiac catheter is constructed to enable said first indifferent electrode to be located outside said heart and adjacent an outer wall of the atrium in a position which overlies said pair of intracardiac atrial sense and pace electrodes to reduce detection of myopotentials and ventricular signals by an atrial sensing channel of said pacemaker.

8. The apparatus as defined in claim 7, further including means for using said first indifferent electrode as only an atrial sensing indifferent electrode.

9. The apparatus as defined in claim 8, wherein said pacemaker includes means for enabling said pacemaker to act as an atrial pacing indifferent electrode.

10. The apparatus as defined in claim 8, further including a second extracardiac catheter connected to said pacemaker and including a second indifferent electrode, said apparatus further including means for using said second indifferent electrode as a ventricle pacing and sensing indifferent electrode and an atrial pacing indifferent electrode.

11. The apparatus as defined in claim 6, wherein said pacemaker includes differential processing means for generating an improved sense signal, said first intracardiac electrode and said first indifferent electrode being connected with said differential processing means.

* * * * *